(12) United States Patent
Tang

(10) Patent No.: US 7,704,536 B2
(45) Date of Patent: *Apr. 27, 2010

(54) ACID-NEUTRALIZING AGENT

(76) Inventor: Tieh-Chun Tang, 1170 Centre Dr., #J, City of Industry, CA (US) 91789

( * ) Notice: Subject to any disclaimer, the term of this patent is extended or adjusted under 35 U.S.C. 154(b) by 165 days.

This patent is subject to a terminal disclaimer.

(21) Appl. No.: 11/906,266

(22) Filed: Oct. 1, 2007

(65) Prior Publication Data

US 2009/0087392 A1    Apr. 2, 2009

(51) Int. Cl.
    *A23L 1/304*    (2006.01)
(52) U.S. Cl. .......................... 426/74; 426/599
(58) Field of Classification Search .................. 426/74, 426/599
    See application file for complete search history.

(56) References Cited

U.S. PATENT DOCUMENTS

| | | | | |
|---|---|---|---|---|
| 1,896,403 | A * | 2/1933 | Haden | 423/173 |
| 2,097,979 | A * | 11/1937 | Horton | 423/173 |
| 2,200,325 | A * | 5/1940 | Botkin et al. | 156/1 |
| 3,622,379 | A * | 11/1971 | Graham et al. | 427/4 |
| 6,508,699 | B1 * | 1/2003 | Santoriello et al. | 452/99 |
| 2005/0226830 | A1 * | 10/2005 | Fang | 424/63 |
| 2007/0160674 | A1 * | 7/2007 | Nakahara et al. | 424/489 |

OTHER PUBLICATIONS www.lime.org. "Using Lime for Acid Neutralization" Sep. 2001, p. 1-2.*
www.wisegeek.com/what-is-sandblasting.htm, Mar. 14, 2006, p. 1-2.*
www.pearl-guide.com/nacre, Aug. 17, 2004, p. 1-2.*
Washington, Antacids and Anti-Reflux Agents, Aug. 2, 1991, ISBN 0-8493-5444-7, p. 2-4.*
Arm and Hammer, http://web.archive.org/web/20040426051919/http://www.armhammer.com/basic/magic, Apr. 26, 2004, p. 1.*

* cited by examiner

*Primary Examiner* — Helen F Pratt
(74) *Attorney, Agent, or Firm* — Gary C. Honeycutt

(57) ABSTRACT

Acid-neutralizing agent contains substantial amount of calcium of an acid-neutralizing ability against various acid chemicals substance for humans, animals, agricultural produces, meat and poultry. And the method of producing the same are provided. An environmental friendly high speed and high press scraping treatment is applied to a calcium-containing substance represented by calcium carbonate-containing substances originating from shellfishes, to eliminate heavy metals and other contamination accumulated on the surface. A heating and baking treatment is applied separately to the different said shellfishes and calcium carbonate-containing minerals and charcoal of bamboo to the temperature and maintaining the temperature not less then the decompose point of each calcium component-containing substance, a sufficient time of heating and baking treatment from 3 hours up to 18 hours depend on materials treated. An ionization and stabilization process is applied to the decomposed calcium components substance in high temperature. A regular pulverizing process is applied to grind the said calcium-containing substance into 500 mesh sizes of powder. A Nano pulverizing process is applied to the said powder into sizes not larger then 18000000 mesh (size of Nano). A formulation process is applied to the different pulverized calcium containing powder in different percentage to formulas which suitable for different applications.

6 Claims, 1 Drawing Sheet

Flow chart of producing acid-neutralizing agent

FIG. 1 - Flow chart of producing acid-neutralizing agent
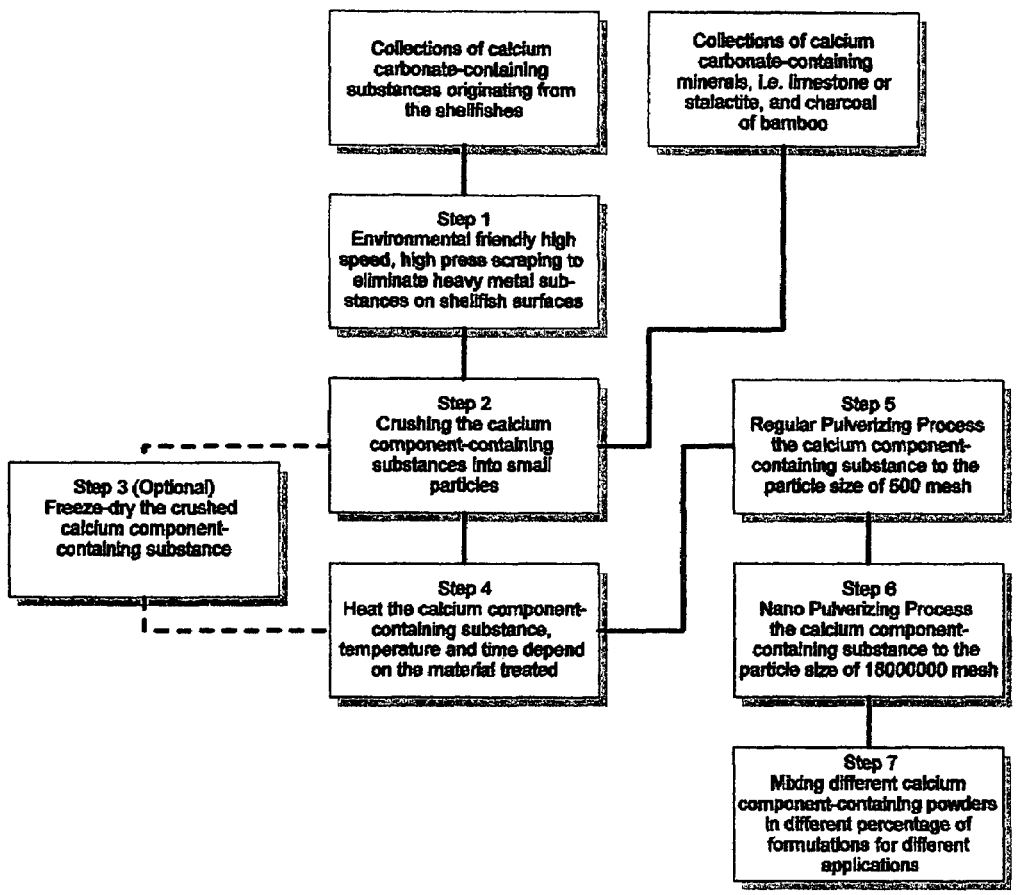

ACID-NEUTRALIZING AGENT

FIELD OF INVENTION

The present invention relates to an acid-neutralizing agent and the methods of producing the same. In particular, the present invention relates to an acid-neutralizing agent of an excellent acid-neutralizing ability against various acids such as acidic fluid and blood in human and animal body, chemical to grown produce such as pesticide, antibiotic and growth hormone.

BACKGROUND

The modern-day lifestyle and diet commonly include having to deal with chemical pollutants in the air, food, drinks, radiation from TV, computers, cell phones and over time working stress, etc. These harmful particles and factors are causing human body's chemistry to become imbalanced and overly acidic, which can result in premature aging, decreased energy, and known slow disease like High Blood Pressure, Diabetes, even Cancers.

The factors that cause a human body's chemistry to become imbalanced and overly acidic are:

1. Air to Breathe—There is no doubt that air pollution has created a great impact to the modern world. Breathing the polluted air will damage a human body's health and make body fluid more and more acidic.

2. Water to Drink—A human body should consist a 70% of water which include blood and body fluid and needs approximately 8 glasses of water a day to stay hydrated and function properly. However, the modern technologies of drinking water such as purified water and Reverse Osmosis Water filtered out all minerals, including minerals that will help to neutralize body acids. The water, by exposed to the air, usually soon turned acidic itself from neutral pH level of 7.0. Drinking these types of water can only make a human body more acidic. Plus, modern life style tends to include many beverages other than regular water, especially kids and teenagers. Most of the beverages available in the market including juice, coffee, cokes and sodas, are extremely acidic which only make an already acidic body even worse.

3. Food to Eat—The conventionally grown fruits, vegetable, meat, poultry, even seafood constantly use chemical compounds such as chemical fertilizer, pesticide, antibiotic and growth hormone to help them grow faster and be more appealing. It means, these chemical compounds are all acidic and stay inside and outside, practically everywhere, of the daily food that modern people intake, which leads to the result of accumulating harmful chemicals, that make a human body more and more acidic.

4. Detergent to Clean—Not a lot of people know that 90% of all commercial soap, shampoos contain Sodium Dodecyl-sulfate (SDS), Sodium Laureth Sulfate (SLES) and/or Sodium Laurel Sulfate (SLS) detergent that can be retained in tissues up to 5 days even after a single drop. These commercial soaps and shampoos do their cleaning function well but the acidic chemicals inside are actually damaging the skin little by little.

5. Radiation and Stress—Modem lifestyles include exposure to technologies like microwaves, TVs, computers and cell phones. The radiation generated by these equipments is damaging human bodies in an un-seeable way. Plus, due to the living pac is much quicker in the modern societies. More and more people are living with heavier stress which also makes their bodies more and more acidic.

These harmful particles and factors are causing the human body's chemistry to become imbalanced and overly acidic, which can result in premature aging, decreased energy, and known slow disease like High Blood Pressure, Diabetes, even Cancers. One simple way resolving all these issues is acid neutralizing.

At late 20th century, more and more people realize the importance of pH level balance to a human body. A healthy body's chemistry should be more alkaline, like 7.5, than acidic. Therefore, how to balance a body's pH level became the newest and most popular studies in all modern societies and the demand of the related health products are dramatically increased.

Acidic chemical compound agents have been applied in our daily lives as food additives, to clean objects, kill germs and bacteria or to prevent effecting from viruses. These acidic chemical compound agents are harmful to human bodies, will generate dioxins and contaminating environments. As examples, which have been used as a food additive in farming and fisheries or marine products industry, there are synthetic anti-bacteria agents, such as sulfamizin, carbadox, or the like, as skin, hair treatment or medicines for human and animals. However, some must be strictly controlled, in particular, in residual value thereof to be less than a standard value, from a view point of safety of foods and medicine.

Therefore, an acid-neutralizing agent made from natural materials as ingredients, rather than agents of chemical compounds mentioned above are required, in particular, in the fields of treating foods, water and beverages which have a possibility to be taken inside the human body through the mouth, and treating cleansing agents which have a possibility to absorbed by human body through skin.

In particular, acid-neutralizing agent made from natural materials containing substantial amount of calcium, such as shellfishes and minerals are harmless when absorbed into the human body, is considered also to have an effect on purification of water. Hereinafter, there are listed examples or cases now in issue.

To produce said acid-neutralizing agent, preparing the said natural materials, in particular shellfishes, generally takes a lot of manpower to wash and scrub, tending to eliminate the died body inside and heavy metal contamination on the surface of shellfish due to environmental pollutions, also takes a lot of time to dry after wash. These factors limited the acid-neutralizing agents' production availability to comply the market demands.

SUMMARY OF THE INVENTION

Therefore, the present invention which uses an environmentally friendly high speed, high pressure scraping treatment can easily and efficiently scratch off the contaminants on the surfaces of the shellfishes, which reduced manpower, time of washing and time of drying, which increases production efficiency to comply the increasing demand.

One aspect of the present invention includes a method for making an improved acid-neutralizing agent, wherein a Nano-pulverizing process is applied to calcium containing substances to yield a powder having nanometer particle size of 0.001 um (18000000 mesh) or smaller, which is close to the size of atom In other words, the contact area of molecules between the acid-neutralizing agent and the acid chemical compound is increased. Therefore, it is possible to obtain a more excellent acid-neutrazing effect. The traditional pulverizing technologies which pulverize calcium component-containing substances normally to the micron size of 1 um (18000 mesh) the maximum. Which calcium carbonate and collagen are still combined and stay in bigger molecule state. Therefore, even the molecule contains amino acids, the absorption to a human body can only reach up to 30% to 40%. Using Nano Technology to pulverize calcium component-containing substances brings the particle size to smaller then 18000000 mesh, which is at least 1000 times smaller then the particle produced by the traditional pulverizing technology, which breaks the amino acids connection between calcium carbonate and collagen, which the absorption rate to a human body can be as high as 99%. For solving the increasing demand problems mentioned above, the present invention of the method of producing an all-natural acid-neutralizing agent which contains substantial amount of calcium made from different shellfishes, an environmental friendly high speed and high press scraping treatment is applied to the shellfishes to eliminate heavy metal contamination accumulated on the surface efficiently which reduced the time and labor dramatically compare with labor washing and long time drying of the traditional way.

The present invention of all-natural acid-neutralizing agent which contains substantial amount of calcium made from any of different shellfishes and calcium carbonate-containing mineral, or a combination of such materials, is obtained by heating the calcium-containing substances in an atmosphere of inactive gas and baking to or above the temperature of from 1100 degree C. to 1300 degree C. for shellfishes, 375 degree C. for pearl, and 1500 degree C. for calcium carbonate-containing minerals, from 3 hours to 18 hours depend on substance treated. When the acid-neutralizing agent mentioned above is Nano Technology pulverized, under the temperature of between −10 degree C. to −50 degree C. to avoid dust explosion due to atom friction, and to have a maximum particle diameter between 10 to the power of −7 to −9 after burned, it can be easily dissolved into water, thereby enabling to further improve its acid-neutralizing effect, and natural calcium particles in this size are absorbable for human body up to 99%.

The baked shellfishes and minerals made from natural material or natural ingredient are described in No. 218 of the list of existing additives, which is defined in the revised version of the Food Hygiene Act and the Nutrition Improvement Act as burned calcium (which mainly contains calcium compounds obtained by burning shells or the like). These are officially recognized to be natural alkaline substances and safe for the human body. As a result of such structure, it is possible to fully neutralize or remarkably reduce the amount of acid level inside and outside of fruits, vegetable, meat, poultry and even human and animal body. Accordingly, regarding an acid-neutralizing agent according to the present invention, it is preferable for it to be used for conditioning drinking water and beverages, neutralizing pesticide and chemical fertilizer inside and on the surface of conventional grown fruits and vegetable, and as raw materials to produce health and skin care products

LIST OF DRAWINGS

FIG. 1—Flow chart of method for producing acid-neutralizing agent

PREFERRED EMBODIMENTS

The acid-neutralizing agent and the method of producing the same according to the present invention will be explained in detail below with reference to the accompanying drawings, as exemplified by preferred embodiments.

The acid-neutralizing agent according to the embodiment of the present invention contains an active ingredient of a heat-treated calcium component-containing substance. The calcium component-containing substance refers to a substance containing calcium or a calcium compound such as calcium oxide, calcium phosphate, calcium carbonate, calcium lactate, and calcium hydroxide.

The calcium component-containing substance is more desirable to use at least one selected from a group consisting of calcium carbonate-containing substances originating from the shellfishes, i.e., Tellinidae, pearl, mother of pearl or the like, coral, calcium carbonate containing minerals, i.e. limestone or stalactite, and charcoal of bamboo. Since the above materials are originally treated as waste or exist naturally, they are available inexpensively and exist abundantly. Therefore, it is possible to produce the acid-neutralizing agent at low cost and, consequently, is possible to inexpensively supply a large amount of the acid-neutralizing agent. Further, it is also possible to decrease a burden to the environment because the amount of the wasted materials is reduced.

Among the above calcium carbonate-containing substances originating from the shellfishes, especially Telliniade, is used as the raw material, it is possible to obtain the acid-neutralizing agent of an excellent acid-neutralizing ability. Therefore, it is desirable to use shellfishes, in particular, the Telliniade.

Another desirable example of the calcium component-containing substance is calcium carbonate-containing minerals, i.e., limestone, stalactite or the like. Since they are all natural product, it is also possible to produce the acid-neutralizing agent at low cost by using it.

The acid-neutralizing agent made by calcium component-containing substance is a mixture of several types of above materials after heat treatment. The acid-neutralizing agent according to the embodiment of the present invention is able to neutralize the number of the chemical compounds such as Diendrin, DDT, Growth Hormone and Antibiotics.

A method of producing the above acid-neutralizing agent will now be explained with reference to FIG. 1 as a flow chart. The production method comprises an environmental friendly high speed and high press scraping Step 1 of scrubbing the surface of the calcium component-containing substance. A crushing Step 2 of crushing the scrubbed calcium component-containing substance into 100 .mu.m to 20 mm. An optional freeze-drying treatment of Step 3 to dry completely the calcium component-containing substance in the degree of −20 degree C. The freeze-drying Step 3 may be performed if necessary. Therefore, the step is depicted with parentheses in FIG. 1. A heat treatment Step 4 includes heating the calcium component-containing substance in an atmosphere of inactive gas, from 375 degrees C. to 1800 degrees C., from 3 hours to 18 hours, depending upon the nature of the starting material, to decompose and ionize the calcium component-containing substances. A regular pulverizing Step 5 of pulverizing the ionized calcium component-containing substance to an average particle size of 500 mesh. A Nano Technology pulverizing Step 6 of pulverizing the calcium component-containing substance into Nano size (particle size between 10 to the power of −7 to −9, not larger then 180000000 mesh). And, the final mixing Step 7 of mixing different calcium component-containing powders in different percentages of formulations to produce products for different applications.

Step 1—Environmental Friendly High Speed, High Pressure Scraping Procedure to Eliminate Accumulated Heavy Metal Contamination on the Surface of Shellfishes When the above calcium carbonate-containing substances originating from the shellfishes, i.e., at least one selected from the group consisting of Tellinidae, pearl mother of pearl or the like, coral calcium carbonate-containing minerals, i.e. limestone or stalactite, surface contaminants adhered thereto are removed at first in the environmental friendly high speed and high press scraping Step 1 using equipment currently available from KC Denmark. Without the scraping Step 1, the heavy metal contamination and malodor is generated in the heat treatment Step 4. Originating from the pieces of meat, the organic matters or the like which are adhered to the calcium carbonate-containing substance originating from the shellfishes, the residual matter remains in the acid-neutralizing agent in some cases. As a result, the acid-neutralizing ability of the acid-neutralizing agent is not excellent in some cases. Further, a heat-generating element or the like of a heat treatment apparatus may be damaged in a short period of time.

The scraping procedure of Step 1 includes mounting the shells in a fixed position, and a high-pressure sandblasting step, using natural sand or pulverized granite, mixed with 5% to 7% of water, supplied with a nozzle pressure of 85 to 90 psi at or near room temperature, and a flow rate of 1.5 GPM to 2.5 GPM. The required time is usually from 5 minutes to one hour, depending upon the nature and the amount of contamination. The angle of impact can be varied during the procedure, to accelerate complete removal of all contaminants.

Step 2—Crushing the Calcium Component-Containing Substances into Small Particles for More Efficient Result on Freeze-Drying Step 3 and Heating Step 4

In this step, the calcium component-containing substance is reduced to an average particle size of 100 .mu.m to 20 mm.

Step 3 (Optional)—Freeze-Dry the Crushed Calcium Component-Containing Substance

When the calcium component-containing substance is crushed to have such a particle size, the particles of the calcium component-containing substance are freeze-dried uniformly in a short period of time over the range from the surface thereof to the inside in the freeze drying treatment Step 3. If the calcium component-containing substance is crushed to be larger than 20 mm, it will take longer to completely dry the calcium component-containing substance since the water in shellfishes is not removed yet at this stage.

It is not necessary to perform the freeze-drying Step 3 when shellfishes is used which has been left to stand for the elapse of time of not less than two years after removing a living body there from The organic matters or the like adhered to the surface of the clamshell are subjected to efflorescence or deliquescence, thereby being spontaneously removed. That is, when the above shellfishes are used as the raw material, it is not necessary to perform the freeze-drying Step 3.

Step 4—Heat and Bake the Calcium Component-Containing Substance, Temperature and Time Depend on the Material Treated Subsequently, in the heat treatment Step 4, the calcium component-containing substances are heat-treated. The heat-treated calcium component-containing substances develop the acid-neutralizing ability in an atmosphere of inactive gas. The inactive gas is preferably nitrogen. The temperature and the time of the heat treatment in Step 4 are determined by type of the calcium component-containing substance to be used as the raw material. For example, pearl is preferably heated for 2 hours when the temperature reaches 375 degree C., to decompose some of its calcium components, and then the temperature is increased to 1100 degrees C. for one hour to ionize the calcium components, using the electrons in the outer shell of the nitrogen gas.

Mother of pearl is preferably heated for 6 hours at a temperature of 1100 degrees C. to decompose some of its calcium components, and then the temperature is increased to 1800 degrees C. for 4 hours to ionize the calcium components, using the electrons in the outer shell of the nitrogen gas.

Tellinidae is preferably heated for 8 hours at a temperature of 1200 degrees C., to decompose some of its calcium components, and then the temperature is increased to 1800 degrees C. for 4 hours, to ionize the calcium components, using the electrons in the outer shell of the nitrogen gas.

Coral is preferably heated for 8 hours at a temperature of 1300 degrees C., to decompose some of its calcium components, and then the temperature is increased to 1800 degrees C. for 6 hours, to ionize the calcium components, using the electron in the outer shell of the nitrogen gas.

Limestone is preferably heated for 12 hours at a temperature of 1500 degrees C., to decompose some of its calcium components, and then the temperature is increased to 1800 degrees C., to ionize the calcium components, using the electron in the outer shell of the nitrogen gas.

In each of the examples above, if the temperature were significantly lower then specified for each different substance; or if the heat treatment times were significantly less then specified, the maximum level of acid-neutralizing ability in the final product would not be obtained.

Step 5—Regular Pulverizing of the Calcium Component-Containing Substances to a Particle Size of 500 mesh Subsequently, in the regular pulverizing step 5, the calcium component-containing substance is pulverized so as to obtain the acid-neutralizing agent until the average particle size thereof is 500 mesh in the first stage of pulverizing.

Step 6—Nano Pulverizing Process the Calcium Component-Containing Substance to a Particle Size of 18000000 mesh The Nano-Technology Pulverize process (equipment currently available from Hsin-Fang Co., Ltd.), operates at temperature of −10 degree C. to −50 degree C. to avoid dust explosion due to atom friction, to the particle size in between 10 to the power of −7 to −9 (18000000 mesh.). The Nano Technology pulverization to obtain fine particles necessarily increases the total surface area of the acid-neutralizing agent. In other words, the contact area of molecules between the acid-neutralizing agent and the acid chemical compound is increased. Therefore, it is possible to obtain a more excellent acid-neutralizing effect. The traditional pulverizing technologies which pulverize calcium component-containing substances normally to the particle size of 18000 mesh (1 um) the maximum. Which calcium carbonate and collagen are still combined and stay in bigger molecule state. Therefore, even the molecule contains amine acids, the absorption to a human body can only reach up to 30% to 40%. Using Nano Technology to pulverize calcium component-containing substances brings the particle size to smaller then 18000000 mesh (0.001 um), which is at least 1000 times smaller then the particle produced by the traditional pulverizing technology, which breaks the amine acids connection between calcium carbonate and collagen, which the absorption rate to a human body can be as high as 99%.

Step 7—Mixing Different Calcium Component-Containing Powders in Different Percentage of Formulations for Different Applications Accordingly, to different percentage of formulations of mixing the fine powder, regarding an acid-neutralizing agent according to the present invention, it is preferable for it to be used for conditioning drinking water and beverages for human body to neutralize acids in blood and body fluid, neutralizing pesticide and chemical fertilizer inside and on the surface of conventional grown fruits and vegetable, chemical compounds such as growing hormone and antibiotic of poultry and meat, chemical contamination of shellfishes and fish, and as raw materials to produce health and skin care products for humans and animals.

The following Examples are meant to illustrate suitable formulas, without limiting the scope of the invention The inventive result is obtained by adding the agent of the invention to any drink formula, any shampoo, and any gum care product.

1. The formula of drink containing the acid-neutralizing agent of the invention.
   Pure Honey 70%
   Malt Dextrin 10%
   Calcium Containing Acid Neutralizing Agent 20%

2. The formula of shampoo containing the acid-neutralizing agent of the invention.
   Calcium Containing Acid Neutralizing Agent 9%
   Pearl Powder 1%
   Glycerin 10%
   Coconut Oil 8%
   Aqua 10.3%
   Palmitic Acid 10%
   Myristic Acid 8%
   Stearic Acid 8%
   Sorbitol 8%
   Propylene Glycol 8%
   Sodium Hydroxide 6.5%
   Lauric Acid 6%
   Sucrose 6%
   Sage Essential Oil 1%
   Sodium Chloride 0.2%

3. The formula of gum care product containing the acid-neutralizing agent of the invention.
   Calcium Containing Acid Neutralizing Agent 8%
   Calcium Carbonate 76.28%
   Sodium Monofluorophosphate 0.79%
   Sirica SI02 18%
   Flavor Oil 1.5%
   Galla Chinensis 1.5%
   Sodium Lauryl Sulfate 3.43%

It has also been discovered that the nanocalcium powder of the invention can be dispersed in water to form a stable suspension having unusually high concentrations of calcium. For example, concentrations up to 25% powder and 75% water by wt. are possible, even without a stabilizing agent. With a stabilizing agent, nanocalcium powder concentrations of 60% by wt. and higher are possible. For purposes of this disclosure, "nanocalcium powder" is defined as comprising an insoluble calcium compound pulverized to a particle size substantially less than one micron. For example, in the range of one nanometer to about 500 nanometers.

A "stable suspension" is defined as a suspension that does not settle appreciably upon standing for 12 hours or more. Upon standing for several days, without a stabilizing agent, some of the calcium powder may settle to the bottom of the container. It may then be difficult to re-disperse the powder by shaking the container. With a stabilizing agent, and with high concentrations of powder, some settling may still occur. But the stabilizing agent permits the powder to be re-dispersed with ease. This second function of the stabilizer is very important. Without it, a permanent separation of some powder could occur, thereby severely limiting the commercial acceptance of the product.

The stable suspension of the invention usually includes a range of particle sizes outside the colloidal range, and also within the colloidal range (less than 200 nanometers). Thus the suspension is in part a colloid, and to that extent it is considered permanently stable without the addition of a stabilizer.

Suitable stabilizing agents are selected from natural fruit juices and natural vegetable juices. The alkaline (alkalizing) juices are preferred. They include the following juices:

| apple | grape | raspberry | cauliflower | lettuce |
|---|---|---|---|---|
| apricot | grapefruit | rhubarb | celery | mushrooms |
| avocado | honeydew | strawberry | chlorella | mustard greens |
| banana | lemon | tangerine | collard greens | onion |
| blackberry | lime | tomato | cucumber | pepper |
| blueberry | muskmelon | plum | dulce | pumpkin |
| cantaloupe | nectarine | watermelon | eggplant | radish |
| cherry | orange | beets | garlic | rutabaga |
| coconut | peach | broccoli | green beans | spinach |
| currant | pear | cabbage | green peas | sweet potato |
| fig | pineapple | carrot | kale | watercress |

The required amount of stabilizer is usually from one to ten percent by wt, and preferably three to seven percent of the total product, by wt. Apple cider vinegar and baking soda are also useful stabilizers.

As a stable suspension, the nanocalcium liquid is much more convenient to use than the dry powder form. For example, it can be packaged in a pump-spray bottle, for washing fresh fruits and vegetables, meat, poultry, fish, and other foods. It will remove surface contaminants, and also kill any harmful bacteria that may be present. In a spray bottle, 3% calcium powder by wt. and 97% water is a convenient ratio.

Also, the liquid form is more readily carried in the purse or pocket, and more conveniently measured, when adding the product to beverages and foods.

The liquid nanocalcium is also useful for external treatment of skin irritations, including insect bites, to reduce itching. It is also useful when added to ordinary skin lotions and creams, to improve quality and smoothness.

What is claimed is:

1. A method of producing an acid-neutralizing agent in the form of a stable aqueous suspension suitable for human consumption, comprising:
   sandblasting a calcium-containing material to eliminate heavy metals and other contamination on the surface;
   crushing the material to an average particle size in the range of 100 microns to 20 mm;
   heating the crushed material a temperature above 1100 deg. C in the presence of nitrogen to cause ionization;
   nano-pulverizing the resulting material to form a powder having a particle size in the nanometer range; and then
   mixing the nano-pulverized powder with water and three to seven percent by wt. of a stabilizer selected from apple cider vinegar, an alkalizing fruit juice, and a vegetable juice, to form a stable suspension.

2. The method of claim 1 wherein the calcium-containing material is selected from limestone, stalactite, charcoal of bamboo, and various seashells, including Tellinidae, pearl, mother of pearl, and coral.

3. An acid-neutralizing agent produced in accordance with claim 2.

4. The method of claim 1 wherein the scraping procedure includes a high-pressure sandblasting step at 85 to 90 psi.

5. An acid-neutralizing agent produced in accordance with claim 3.

6. An acid-neutralizing agent produced in accordance with the method of claim 1.

* * * * *